(12) United States Patent
Le Devedec et al.

(10) Patent No.: US 12,064,461 B2
(45) Date of Patent: Aug. 20, 2024

(54) DEEP PENETRATING TOPICAL CANNABINOID COMPOSITIONS AND METHODS FOR TREATING MUSCULOSKELETAL INFLAMMATION AND PAIN

(71) Applicant: Avicanna Inc., Toronto (CA)

(72) Inventors: Frantz Henri Emmanuel Le Devedec, North York (CA); Aras Azadian, Toronto (CA); Setu Nimish Purohit, Toronto (CA)

(73) Assignee: Avicanna Inc., Toronto (CA)

( * ) Notice: Subject to any disclaimer, the term of this patent is extended or adjusted under 35 U.S.C. 154(b) by 0 days.

(21) Appl. No.: 17/811,972

(22) Filed: Jul. 12, 2022

(65) Prior Publication Data
US 2023/0025693 A1    Jan. 26, 2023

Related U.S. Application Data

(60) Provisional application No. 63/203,294, filed on Jul. 16, 2021.

(51) Int. Cl.
| | | |
|---|---|---|
| *A61K 36/185* | (2006.01) | |
| *A61K 9/06* | (2006.01) | |
| *A61K 31/047* | (2006.01) | |
| *A61K 31/25* | (2006.01) | |
| *A61K 31/717* | (2006.01) | |
| *A61K 31/78* | (2006.01) | |

(52) U.S. Cl.
CPC .............. *A61K 36/185* (2013.01); *A61K 9/06* (2013.01); *A61K 31/047* (2013.01); *A61K 31/25* (2013.01); *A61K 31/717* (2013.01); *A61K 31/78* (2013.01)

(58) Field of Classification Search
CPC ...... A61K 36/185; A61K 9/06; A61K 31/047; A61K 31/25; A61K 31/717; A61K 31/78; A61K 47/10; A61K 9/1075; A61K 9/0014; A61K 47/32; A61P 21/00
See application file for complete search history.

(56) References Cited

U.S. PATENT DOCUMENTS

| | | | |
|---|---|---|---|
| 2010/0273895 A1* | 10/2010 | Stinchcomb | A61P 17/14 514/733 |
| 2021/0093539 A1* | 4/2021 | LaRosa | A61K 8/416 |
| 2021/0115748 A9* | 4/2021 | Rome | A61K 47/44 |

FOREIGN PATENT DOCUMENTS

WO    WO-2021023351 A1 *   2/2021   ............ A61K 31/05

OTHER PUBLICATIONS

Bonacucina, et al., "Characterization and stability of emulsion gels based on acrylamide/sodium acryloyldimethyl taurate copolymer," Aaps Pharmscitech 10, 2009, pp. 368-375.

* cited by examiner

*Primary Examiner* — Robert A Wax
*Assistant Examiner* — Quanglong N Truong
(74) *Attorney, Agent, or Firm* — DLA PIPER LLP (US); Dennis J. Parad

(57) ABSTRACT

Topical compositions comprising cannabinoids in combination with one or more humectants and one or more penetration enhancers are provided. Also provided are methods comprising applying a topical cannabinoid composition provided herein to the skin areas of a subject affected by inflammation and/or pain associated with musculoskeletal disease or condition and uses of a topical cannabinoid formulation provided herein for the treatment of inflammation and/or pain associated with musculoskeletal disease or condition in a subject.

20 Claims, 3 Drawing Sheets

DEEP PENETRATING TOPICAL CANNABINOID COMPOSITIONS AND METHODS FOR TREATING MUSCULOSKELETAL INFLAMMATION AND PAIN

CROSS-REFERENCE TO RELATED APPLICATIONS

This application claims priority to U.S. Provisional Application No. 63/203,294, filed Jul. 16, 2021, which is herein incorporated by reference in its entirety.

FIELD

The present disclosure relates to compositions comprising one or more cannabinoids for topical application.

BACKGROUND

Pain generates from nociceptors responding to stimuli by sending nerve signals to the spinal cord and brain. Such signals may be indicative of tissue irritation, impending injury, or actual injury, and are often characterized as aching and/or direct pains. Examples of conditions associated with nociceptive pain include bone fractures, burns, bumps, bruises, inflammation (from an infection or arthritic disorder), arthralgia, general myalgia and more specific myalgia caused by symptoms categorized generally as amplified musculoskeletal pain (AMP) syndrome.

Although various drugs are currently available to alleviate pain, most painkillers have modest or limited efficacy and are associated with various debilitating side effects. Side effects of non-steroidal anti-inflammatory drugs include gastrointestinal and liver damage while the administration of opiates may induce tolerance and addiction. Thus, better therapies are needed for the management of pain.

With relaxation of laws regulating *cannabis* use, there now exists the opportunity to explore the potential of cannabinoids for treating pain associated with musculoskeletal disorders such as rheumatoid arthritis and osteoarthritis.

In addition, there remains a need for improved topical formulations to provide pain relief, in particular improved formulations for the delivery of active ingredients directly in deep tissues to provide better efficacy and reduced gastrointestinal, central nervous system and cardiovascular side effects associated with oral forms.

SUMMARY

In one aspect, there is provided a topical cannabinoid composition comprising:
  a. a cannabinoid at 0.01-10% (w/w),
  b. a humectant at 0.01-10% (w/w),
  c. a penetration enhancer at 1-5% (w/w), and
  d. water to make up 100% by weight,
  wherein the topical cannabinoid composition comprises less than 10% (w/w) of glycol ether.

In an embodiment of the topical cannabinoid composition as described herein, the topical cannabinoid composition comprises no more than 5% (w/w) of glycol ether.

In an embodiment of the topical cannabinoid composition as described herein, the topical cannabinoid composition comprises no more than 0.25% (w/w) of glycol ether.

In another aspect, there is provided a topical cannabinoid composition comprising:
  a. a cannabinoid at 0.01-10% (w/w),
  b. a humectant at 0.01-10% (w/w),
  c. a penetration enhancer at 1-5% (w/w), and
  d. water at no less than 31% (w/w).

In an embodiment of the topical cannabinoid composition as described herein, at least one of the humectants and the penetration enhancers has a molecular weight lower than the molecular weight of the cannabinoid.

In an embodiment of the topical cannabinoid composition as described herein, the humectant is 1,3-butylene glycol, and the penetration enhancer is diethylene glycol monoethyl ether.

In an embodiment of the topical cannabinoid composition as described herein, the cannabinoid is cannabidiol (CBD), cannabidiolic acid (CBDA), cannabidivarin (CBDV), cannabigerol (CBG), cannabigervarin (CBGV), tetrahydrocannabivarin (THCV), tetrahydrocannabinol (THC), or any combination thereof.

In an embodiment of the topical cannabinoid composition as described herein, the cannabinoid is cannabidiol (CBD).

In an embodiment of the topical cannabinoid composition as described herein, the composition further comprises an emulsifier at 1-10% (w/w).

In an embodiment of the topical cannabinoid composition as described herein, the emulsifier is Sepineo™ P600.

In an embodiment of the topical cannabinoid composition as described herein, the composition has a pH of 4-7.

In an embodiment of the topical cannabinoid composition as described herein, the composition further comprises one or more of:
  a. a surfactant at 0.5-5% (w/w),
  b. a second penetration enhancer at 0.1-3% (w/w),
  c. a cooling sensation enhancer at 0.5-2.5% (w/w),
  d. a preservative at 0.1-3% (w/w),
  e. an antioxidant at 0.1-3% (w/w),
  g. a third penetration enhancer at 1-5% (w/w), and
  h. water to make up 100% by weight.

In an embodiment of the topical cannabinoid composition as described herein, the surfactant is Polysorbate 80, the second penetration enhancer is clove oil, the cooling sensation enhancer is menthol, the preservative is phenoxyethanol, the anti-oxidant is butylated hydroxytoluene (BHT), and the third penetration enhancer is oleic acid.

In an embodiment of the topical cannabinoid composition as described herein, the composition is a cream, ointment, gel, lotion, liquid, solution, spray, aerosol, patch or any other dosage form suitable for topical application, or any combination thereof.

In an embodiment of the topical cannabinoid composition as described herein, the composition is a gel.

In another aspect, there is provided a deep tissue gel comprising:
  a. a cannabinoid at 0.01-10% (w/w),
  b. a cannabinoid deep penetration aiding agent at 0.1-10% (w/w), and
  c. water to make up 100% by weight.

In another aspect, there is provided a method comprising applying the topical cannabinoid composition as described herein to the skin areas of a subject affected by inflammation and/or pain associated with musculoskeletal disease or condition.

In an embodiment of the method as described herein, the skin areas of a subject are knee joints; proximal interphalangeal (PIP) and metacarpophalangeal (MCP) joints of the hands; wrist joints; small joints of the feet including the metatarsophalangeal (MTP) joints; shoulder joints; elbow joints; neck joints; rib cage; upper back; lower back; hips; buttocks; thighs; ankle joints; heels and toes.

In an embodiment of the method as described herein, the musculoskeletal disease or condition is: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

In another aspect, there is provided use of the topical cannabinoid formulation described herein for the treatment of inflammation and/or pain in a subject.

In an embodiment of the use as described herein, the inflammation and/or pain is due to rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

Other aspects, features, and embodiments of the present disclosure will become apparent to those of ordinary skill in the art upon review of the following description of specific embodiments in conjunction with the accompanying figures.

BRIEF DESCRIPTION OF THE FIGURES

Compositions provided herein, in accordance with one or more various embodiments, are described in detail with reference to the following figures. The drawings are provided for the purposes of illustration only and merely depict typical or example embodiments of the disclosed compositions.

DETAILED DESCRIPTION

Figure 1:
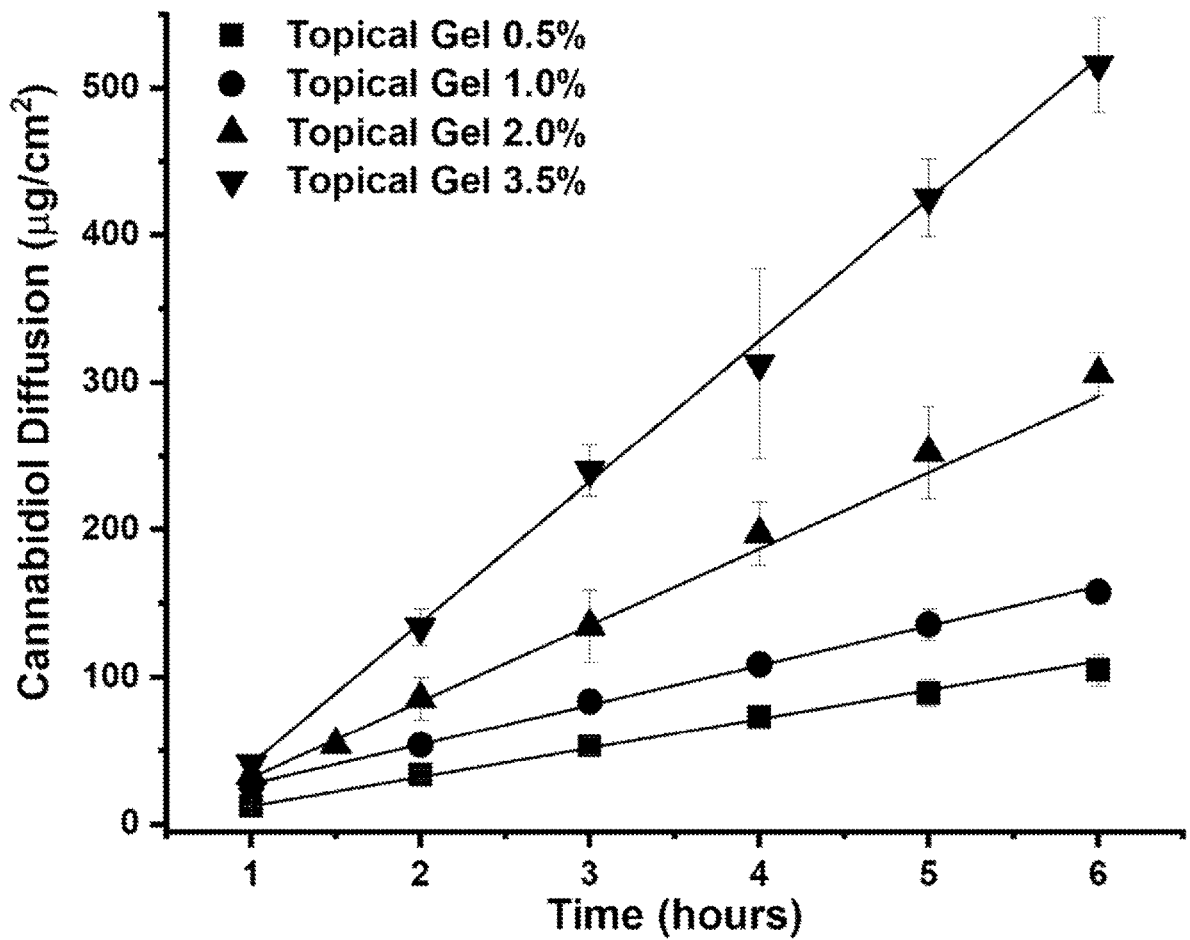
FIG. 1 illustrates CBD diffusion/release from the composition A with various CBD content of 0.5, 1.0, 2.0 and 3.5% w/w. CBD diffusion/release obtained under sink conditions through cellulose acetate membrane at 32° C.-600 rpm; n=6 for each evaluation.

It has been discovered by the present inventors that the cannabinoid or combination of cannabinoids comprised in compositions provided herein, upon topical application, is available at the site of administration in a mammal in a therapeutically effective amount and are absorbed in the deeper layers of skin in a therapeutically effective concentration. Compositions provided herein comprise the combination of humectants and penetration enhancers, which are selected such that these ingredients not only improve penetration of cannabinoids into the epidermis, but they also enter the sub-epidermal layers (such as dermis and hypodermis layers) quickly with the resulting effects that transportation/diffusion of cannabinoids through the sub-epidermal layers of the skin is enhanced.

It is expected that compositions provided herein would have less frequency and severity of side-effects associated with oral and systemic cannabinoid administration because the amount of cannabinoids circulating in a subject should be reduced due to first bypass of portal circulation.

Provided herein are topical compositions comprising cannabinoids which penetrate into the epidermis of the skin and further penetrates into the sub-epidermal layers (such as dermis and hypodermis layers) following application to the skin for a sufficient time to be absorbed and have a therapeutic effect trans dermally, e.g., through deep tissues of the skin.

Compositions provided herein may be useful for treating inflammation and/or pain due to musculoskeletal diseases and conditions including, but not limited to, rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

Compositions provided herein can also be used in conjunction with available treatments of musculoskeletal diseases.

Topical cannabinoid compositions provided herein exhibit excellent overall stability and viscosity.

"Cannabinoid," as used herein, is meant to include compounds which interact with the cannabinoid receptor and various cannabinoid mimetics, such as cannabidiol (CBD), cannabidiolic acid (CBDA), cannabidivarin (CBDV), cannabigerol (CBG), cannabigervarin (CBGV), tetrahydrocannabivarin (THCV) and tetrahydrocannabinol (THC).

"Phytocannabinoids" as used herein means cannabinoids extracted from *Cannabis* plant species including by the way of non-limiting example *Cannabis sativa, Cannabis indica* and *Cannabis ruderalis* and all resins, stalks, flowers, seeds, and oils related thereto.

The term "active agent" is generally understood to mean an active pharmaceutical ingredient.

The terms "topical composition" or "topical formulation" mean a composition in which an active agent may be placed for direct application to a skin surface and from which a therapeutically effective amount of the active agent may be released. Such formulations may include creams, ointments, gels, lotions, or any other dosage form suitable for topical application.

The terms "skin" or "skin surface" is meant to include the outer skin of a subject comprising one or more epidermal layers.

As used herein, the term "gel" means a jelly-like material that can have properties ranging from soft and fluid to hard and tough. Gels can be in a liquid, a semi-liquid, a semi-solid or a solid state. Solid gels are defined as a substantially diluted cross-linked system, which exhibits no flow when in the steady state. By weight, gels are mostly liquid, yet they behave like semi-solids due to a three-dimensional cross-linked network of a solidifying, gelling or thickening agent within the liquid.

The term "therapeutically effective amount" or "therapeutically and/or prophylactically effective amount" as used herein refers to an amount of compound or agent that is sufficient to elicit the required or desired therapeutic and/or prophylactic response, as the particular treatment context may require. It will be understood that a therapeutically and/or prophylactically effective amount of an active agent for a subject is dependent inter alia on the body weight of the subject as well as other factors known to a person of ordinary skill in the art.

The terms "treat," "treating," or "treatment of" are used herein in their broad senses unless otherwise specifically indicated in the particular context, and results of a treatment may generally include reversing, alleviating, or inhibiting the progress of an indicated disorder or condition, or one or more symptoms of the disorder or condition.

"wt %" or "w/w %" when referring to the percentage of a component in a composition is percentage of the weight of the component in the composition relative to the total weight of the composition.

The term "excipient" herein means any substance, not itself an active agent, which may be used as a carrier or vehicle for delivery of an active agent to a subject or combined with an active agent to improve its handling or storage properties or to permit or facilitate formation of a dose unit of the composition. Examples of excipients include, but are not limited to, a "humectant", which is capable of attracting or retaining moisture; a "penetration enhancer", which is capable of improving penetration of an active agent into the epidermis; an "emulsifier" or "emulsifying agent", which is capable of lowering surface tension between a non-polar and polar phase; a "surfactant", which lowers the surface tension (or interfacial tension) between two liquids, between a gas and a liquid, or between a liquid and a solid; a "cooling sensation enhancer", which provides cooling effect to the skin by acting on sensory nerve endings present in skin; a "preservative", which prevents decomposition of composition by microbial growth or by undesirable chemical changes; and an "antioxidant" refers to a substance that inhibits oxidation or reactions promoted by oxygen or peroxides.

As used herein, the term "stable," when referring to a composition, means that the composition can be cycled weekly between freezer and ambient room temperature conditions for a minimum of 1 month while retaining its pH and viscosity within defined ranges.

"Alleviate" as used herein, is meant to include complete elimination as well as any clinically or quantitatively measurable reduction in the subject's symptoms and/or discomfort.

A "subject" herein to which a therapeutic agent or composition thereof can be administered includes mammals such as a human subject of either sex and of any age, and also includes any nonhuman animal, particularly a domestic or companion animal such as a cat, dog or horse, as well as laboratory animals such as guinea pigs.

As discussed in greater detail in the illustrative and non-limiting examples provided herein, the present disclosure is directed to topical formulations/compositions that incorporate at least one cannabinoid.

In one aspect, there is provided a topical cannabinoid composition comprising:
 a. a cannabinoid at 0.01-10% (w/w),
 b. a humectant at 0.01-10% (w/w),
 c. a penetration enhancer at 1-5% (w/w), and
 d. water to make up 100% by weight,
wherein the topical cannabinoid composition comprises less than 10% (w/w) of a glycol ether. As used herein, a concentration of a component referred herein is a total concentration when a topical cannabinoid composition provided herein comprises two or more compounds that are considered to belong to the same component (e.g., for a topical cannabinoid composition comprising a mixture of tetrahydrocannabinol and cannabidiol, both cannabinoids, 5% (w/w) of a cannabinoid is the total concentration of the mixture of tetrahydrocannabinol and cannabidiol).

In certain exemplary, non-limiting embodiments, a topical cannabinoid composition provided herein comprises less than 9%, less than 5%, less than 1%, less than 0.5%, or less than 0.25% of the glycol ether.

In another aspect, there is provided a topical cannabinoid composition comprising:
 a. a cannabinoid at 0.01-10% (w/w),
 b. a humectant at 0.01-10% (w/w),
 c. a penetration enhancer at 1-5% (w/w), and
 d. water at no less than 31% (w/w).

In certain exemplary, non-limiting embodiments, a topical cannabinoid composition provided herein comprises water at no less than 35% (w/w), 40% (w/w), 45% (w/w), 50% (w/w), 55% (w/w), 60% (w/w), 65% (w/w), 70% (w/w), 75% (w/w), 80% (w/w), 85% (w/w), 90% (w/w), 91% (w/w), 92% (w/w), 93% (w/w), 94% (w/w), 95% (w/w), 96% (w/w), 97% (w/w), or 98% (w/w).

In another aspect, there is provided a deep tissue gel comprising:
 a. a cannabinoid at 0.01-10% (w/w),
 b. a cannabinoid deep penetration aiding agent at 0.1-10% (w/w), and
 c. water to make up 100% by weight.

As used herein, the term "cannabinoid deep penetration aiding agent" includes one or more compounds or materials that can move through the epidermis of skin to reach the sub-epidermal layers more quickly than a cannabinoid in the gel when the gel is applied to the skin, and can enhance, improve or speed up the movement of the cannabinoid into and through the sub-epidermal layers, thereby increasing transportation/diffusion of the cannabinoid through the sub-epidermal layers. In an embodiment, a combination of humectant and penetration enhancers can serve as a cannabinoid deep penetration aiding agents when the humectant and penetration enhancers are selected such that the combination not only improves penetration of cannabinoids into the epidermis, but also enters the sub-epidermal layers (such as dermis and hypodermis layers) quickly with the resulting effects that transportation/diffusion of cannabinoids through the sub-epidermal layers of the skin is enhanced. In another embodiment, cannabinoid deep penetration aiding agents include a combination of a humectant and a penetration enhancers selected as described above, further in combination with an emulsifier selected for emulsifying the cannabinoid in or on the epidermis.

Exemplary cannabinoids include cannabidiol (CBD), cannabidiolic acid (CBDA), cannabidivarin (CBDV), cannabigerol (CBG), cannabigervarin (CBGV), tetrahydrocannabivarin (THCV), tetrahydrocannabinol (THC), combinations, and mixtures thereof extracted from *Cannabis* plant species including *Cannabis sativa, Cannabis indica* and *Cannabis ruderalis* and all resins, stalks, flowers, seeds and oils related thereto.

In certain exemplary, non-limiting embodiments, a topical cannabinoid composition provided herein may include about 0.01% to about 10% (w/w) of cannabinoid(s). For example, a topical cannabinoid composition provided herein may comprise about 0.1% to about 10%, about 0.5% to about 10%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0.01% to about 9%, about 0.1% to about 9%, about 0.5% to about 9%, about 1% to about 9%, about 2% to about 9%, about 3% to about 9%, about 4% to about 9%, about 5% to about 9%, about 6% to about 9%, about 7% to about 9%, about 8% to about 9%, about 0.01% to about 8%, about 0.1% to about 8%, about 0.5% to about 8%, about 1% to about 8%, about 2% to about 8%, about 3% to about 8%, about 4% to about 8%, about 5% to about 8%, about 6% to about 8%, about 7% to about 8%, about 0.01% to about 7%, about 0.1% to about 7%, about 0.5% to about 7%, about 1% to about 7%, about 2% to about 7%, about 3% to about 7%, about 4% to about 7%, about 5% to about 7%, about 6% to about 7%, about 0.01% to about 6%, about 0.1% to about 6%, about 0.5% to about 6%, about 1% to about 6%, about 2% to about 6%, about 3% to about 6%, about 4% to about 6%, about 5% to about 6%, about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.1% to about 1%, or about 0.5% to about 1% (w/w) of cannabinoid(s).

In certain exemplary, non-limiting embodiments, a topical cannabinoid composition provided herein may comprise at least 0.01%, at least 0.1%, at least 0.5%, at least 1%, at least 2%, at least 3%, at least 4%, at least 5%, at least 6%, at least 7%, at least 8%, at least 9%, or at least 10% (w/w) of cannabinoid(s).

In certain exemplary, non-limiting embodiments, a topical cannabinoid composition provided herein may comprise about 0.01%, about 0.1%, about 0.5%, about 1%, about 2%, about 3%, about 4%, about 5%, about 6%, about 7%, about 8%, about 9%, or about 10% (w/w) of cannabinoid(s).

In certain exemplary, non-limiting embodiments, topical cannabinoid composition provided herein may be provided as cream, ointment, gel, liquid, lotion, solution, spray, aerosol, patch, or combinations thereof.

In certain exemplary, non-limiting embodiments, topical cannabinoid compositions provided herein may be provided as gels. Gels offer ease of application, least irritation to the skin and optimal viscosity that is needed for deep absorption of cannabinoids in the epidermis of the skin, thereby providing beneficial effects on the impacted tissue or the tissue of interest for amelioration of disease conditions.

Without being limited by any particular theory, it is expected that gels would penetrate faster in the skin, facilitating optimal absorption of the active agent into the deeper layers of the skin.

In certain exemplary, non-limiting embodiments, a topical cannabinoid composition may include cannabinoids in a specific therapeutic amount for treating subjects suffering from pain associated with disorders, diseases including but not limited to: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

Other ingredients may be provided in topical cannabinoid compositions provided herein, so long as they are physiologically acceptable and suitable for use in combination with cannabinoids.

In certain exemplary, non-limiting embodiments, a topical cannabinoid composition provided herein may include one or more humectants, which may be a polyol and/or have a molecular weight lower than that of the cannabinoid(s) comprised in the topical cannabinoid composition. Examples of humectants include glycerin, propylene glycol, butylene glycol, dipropylene glycol, pentylene glycol, hexylene glycol, polyethylene glycol, combinations, and mixtures thereof.

In certain exemplary, non-limiting embodiments, a topical cannabinoid composition provided herein may include about 0.01% to about 10% (w/w) of humectant(s). For example, a topical cannabinoid composition provided herein may comprise about 0.1% to about 10%, about 0.5% to about 10%, about 1% to about 10%, about 2% to about 10%, about 3% to about 10%, about 4% to about 10%, about 5% to about 10%, about 6% to about 10%, about 7% to about 10%, about 8% to about 10%, about 9% to about 10%, about 0.01% to about 9%, about 0.1% to about 9%, about 0.5% to about 9%, about 1% to about 9%, about 2% to about 9%, about 3% to about 9%, about 4% to about 9%, about 5% to about 9%, about 6% to about 9%, about 7% to about 9%, about 8% to about 9%, about 0.01% to about 8%, about 0.1% to about 8%, about 0.5% to about 8%, about 1% to about 8%, about 2% to about 8%, about 3% to about 8%, about 4% to about 8%, about 5% to about 8%, about 6% to about 8%, about 7% to about 8%, about 0.01% to about 7%, about 0.1% to about 7%, about 0.5% to about 7%, about 1% to about 7%, about 2% to about 7%, about 3% to about 7%, about 4% to about 7%, about 5% to about 7%, about 6% to about 7%, about 0.01% to about 6%, about 0.1% to about 6%, about 0.5% to about 6%, about 1% to about 6%, about 2% to about 6%, about 3% to about 6%, about 4% to about 6%, about 5% to about 6%, about 0.01% to about 5%, about 0.1% to about 5%, about 0.5% to about 5%, about 1% to about 5%, about 2% to about 5%, about 3% to about 5%, about 4% to about 5%, about 0.01% to about 4%, about 0.1% to about 4%, about 0.5% to about 4%, about 1% to about 4%, about 2% to about 4%, about 3% to about 4%, about 0.01% to about 3%, about 0.1% to about 3%, about 0.5% to about 3%, about 1% to about 3%, about 2% to about 3%, about 0.01% to about 2%, about 0.1% to about 2%, about 0.5% to about 2%, about 1% to about 2%, about 0.1% to about 1%, or about 0.5% to about 1% (w/w) of humectant(s).

In certain exemplary, non-limiting embodiments, a topical cannabinoid composition provided herein may comprise at least 0.01%, at least 0.1%, at least 0.5%, at least 1%, at least 2%, at least 3%, at least 4%, at least 5%, at least 6%, at least 7%, at least 8%, at least 9%, or at least 10% (w/w) of humectant(s).

In certain exemplary, non-limiting embodiments, a topical cannabinoid composition provided herein may comprise about 0.01%, about 0.1%, about 0.5%, about 1%, about 2%, about 3%, about 4%, about 5%, about 6%, about 7%, about 8%, about 9%, or about 10% (w/w) of humectant(s).

In certain exemplary, non-limiting embodiments, a topical cannabinoid composition provided herein may include one or more penetration enhancers which may be a glycol ether, octyldecanol, or isopropyl myristate, and/or have a molecular weight lower than that of the cannabinoid(s) comprised in the topical cannabinoid composition. Examples of penetration enhancers include diethylene glycol monoethyl ether, steareth-20, steareth-2, octyldecanol, isopropyl myristate, combinations, and mixtures thereof.

In certain exemplary, non-limiting embodiments, a topical cannabinoid composition provided herein may include about 1% to about 5% (w/w) of penetration enhancer(s). For example, a topical cannabinoid composition provided herein may comprise about 2% to about 5%, about 3% to about 5%, about 4% to about 5%, about 1% to about 4%, about 2% to about 4%, about 3% to about 4%, about 1% to about 3%, about 2% to about 3%, or about 1% to about 2% (w/w) of penetration enhancer.

In certain exemplary, non-limiting embodiments, a topical cannabinoid composition provided herein may comprise at least 1%, at least 2%, at least 3%, at least 4%, or at least 5% (w/w) of penetration enhancer.

In certain exemplary, non-limiting embodiments, a topical cannabinoid composition provided herein may comprise about 1%, about 2%, about 3%, about 4%, or about 5% (w/w) of penetration enhancer.

In certain exemplary, non-limiting embodiments, both the humectant and the penetration enhancer of a topical cannabinoid composition provided herein have a molecular weight lower than the molecular weight of the cannabinoid. For example, the humectant and/or the penetration enhancer may have a molecular weight between 50 and 300 g/mol, between 75 and 200 g/mol, or between 75 and 150 g/mol. Without being limited by any particular theory, it is expected that the movement of compounds through skin layers, such as sub-epidermal layers, is affected by their molecular size, which is related to their molecular weight, among other factors. Therefore, it is expected to be beneficial to minimize the transport/absorption time of ingredients other than cannabinoids across epidermis into the sub-epidermal layers.

In certain exemplary, non-limiting embodiments, a topical cannabinoid composition provided herein may include an emulsifier, such as carboxymethyl cellulose, or hydroxyethyl cellulose; polyacrylates such as carbomer or carbopol (e.g. Carbopol® 974); polycarbophils such as Noveon® AA-1; polyvinylalcohol such as Mowiol® 26-88; polyvinylpyrrolidone such as Povidone® K30; xanthan gum; acryloyldimethyltaurate polymers such as acrylamide/sodium acryloyldimethyltaurate copolymer (e.g. Sepineo® P600), acrylamide/sodium acryloyldimethyltaurate/acrylic acid copolymer, ammonium acryloyldimethyltaurate/Beheneth-25 methacrylate crosspolymer, ammonium acryloyldimethyltaurate/carboxyethyl acrylate crosspolymer, ammonium acryloyldimethyltaurate/Laureth-7 methacrylate copolymer, ammonium acryloyldimethyltaurate/Steareth-25 methacrylate crosspolymer, ammonium acryloyldimethyltaurate/Steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium scryloyldimethyltaurate/Steareth-20 methacrylate copolymer, hydroxyethyl acrylate/sodium acryloyldimethyl taurate copolymer, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, combinations, and mixtures thereof.

In certain exemplary, non-limiting embodiments, a topical cannabinoid composition provided herein may include about 1% to about 10% (w/w) of emulsifier(s).

In certain exemplary, non-limiting embodiments, a topical cannabinoid composition provided herein may comprise about 1%, about 2%, about 3%, about 4%, about 5%, about 6%, about 7%, about 8%, about 9%, or about 10% (w/w) of emulsifier(s).

In certain exemplary, non-limiting embodiments, a topical cannabinoid composition provided herein may include one or more surfactant(s), such as castor oil derivatives, an ethoxylated fatty alcohol, PEG-1000 monocetyl ether, alkyl trimethyl ammonium bromide, glycerol monostearate, potassium stearate, sodium lauryl sulfate, sodium cetearyl sulfate, saponin, Polysorbate 20 (Tween™ 20), Polysorbate 40 (Tween 40), Polysorbate 60 (Tween 60) and Polysorbate 80 (Tween 80), combinations, and mixtures thereof.

In certain exemplary, non-limiting embodiments, a topical cannabinoid composition provided herein may include about 0.5% to about 5% (w/w) of surfactant(s).

In certain exemplary, non-limiting embodiments, a topical cannabinoid composition provided herein may comprise about 0.5%, about 1%, about 2%, about 3%, about 4%, or about 5% (w/w) of surfactant(s).

In certain exemplary, non-limiting embodiments, a topical cannabinoid composition provided herein may include a second penetration enhancer which may be an essential oil such as anise oil, angelica oil, basil oil, bay oil, bergamot oil, rose oil, camphor oil, cananga oil, cardamom oil, caraway oil, cedar oil, cedarwood oil, Chamaecyparis obtusa oil, chamomile oil, cinnamon oil, citronella oil, clove oil, copaiba balsam oil, cumin oil, clove oil, coriander oil, dill oil, eucalyptus oil, fennel oil, garlic oil, geranium oil, grapefruit oil, ginger oil, guaiac oil, hiba oil, iris oil, Japanese mint oil, jasmine oil, lavender oil, lemon oil, lemongrass oil, linaloe oil, Lindera oil, mandarin oil, mint oil, neroli oil, onion oil, orange oil, oregano oil, palmarosa sofia oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, vetivert oil, western mint oil, wintergreen oil, or any combination thereof.

In certain exemplary, non-limiting embodiments, a topical cannabinoid composition provided herein may include about 0.1% to about 3% (w/w) of a second penetration enhancer.

In certain exemplary, non-limiting embodiments, a topical cannabinoid composition provided herein may comprise about 0.1%, about 1.5%, about 1%, about 1.5%, about 2%, about 2.5% or about 3% (w/w) of a second penetration enhancer.

In certain exemplary, non-limiting embodiments, a topical cannabinoid composition provided herein may include one or more cooling sensation enhancer(s), such as menthol, menthyl acetate, menthone, isomentone, sabinene hydrate, isopulegol, piperitol, p-menthane-3-carboxylic acid amide, p-menthanediol, menthylglucoside, menthyl-2-pyrrolidone-5 Carboxylate, menthyl keto alkanoate, menthyl N-acetylglycine, menthyl hydroxyalkanoate, 2-mentoxytetrahydropyran, 2-mentoxytetrahydrofuran, menthoxypropane-1,2-diol, menthyl 3-hydroxybutyrate, combinations, and mixtures thereof.

In certain exemplary, non-limiting embodiments, a topical cannabinoid composition provided herein may include about 0.5% to about 2.5% (w/w) of cooling sensation enhancer(s).

In certain exemplary, non-limiting embodiments, a topical cannabinoid composition provided herein may comprise about 0.5%, about 1%, about 1.5%, about 2%, or about 2.5% (w/w) of cooling sensation enhancer(s).

In certain exemplary, non-limiting embodiments, a topical cannabinoid composition provided herein may include one or more preservatives, such as ethylparaben, methylparaben, propylparaben, butylparaben, isobutylparaben, benzalkonium chloride, imidurea, phenoxyethanol, combinations, and mixtures thereof.

In certain exemplary, non-limiting embodiments, a topical cannabinoid composition provided herein may include about 0.1% to about 3% (w/w) of preservative(s).

In certain exemplary, non-limiting embodiments, a topical cannabinoid composition provided herein may comprise about 0.1%, about 0.5%, about 1%, about 2%, or about 3% (w/w) of preservative(s).

In certain exemplary, non-limiting embodiments, a topical cannabinoid composition provided herein may include one or more antioxidant(s), such as vitamin B, nordihydroguaiaretic acid, butylated hydroxyanisole (BHA), butylated hydroxytoluene (BHT), propyl gallate, erythorbate acid, sodium erythorbate, ascorbic palmitate, ascorbic stearate, combinations, and mixtures thereof.

In certain exemplary, non-limiting embodiments, a topical cannabinoid composition provided herein may include about 0.1% to about 3% (w/w) of antioxidant(s).

In certain exemplary, non-limiting embodiments, a topical cannabinoid composition provided herein may comprise about 0.1%, about 0.5%, about 1%, about 2%, or about 3% (w/w) of antioxidant(s).

In certain exemplary, non-limiting embodiments, a topical cannabinoid composition provided herein may include third penetration enhancer, such as isopropyl myristate, myristoleic acid, palmitoleic acid, sapienic acid, oleic acid, elaidic acid, vaccenic acid, linoleic acid, linoelaidic acid, arachidonic acid, eicosapentaenoic acid, erucic acid, docosahexaenoic acid, combinations, and mixtures thereof.

In certain exemplary, non-limiting embodiments, a topical cannabinoid composition provided herein may include about 1% to about 5% (w/w) of third penetration enhancer.

In certain exemplary, non-limiting embodiments, a topical cannabinoid composition provided herein may comprise about 1%, about 2%, about 3%, about 4%, or about 5% (w/w) of third penetration enhancer.

In certain exemplary, non-limiting embodiments, a topical cannabinoid composition provided herein may include one or more carriers, such as water, lanolin or lanolin alcohols, mineral oil, fragrant or essential oil, combinations, and mixtures thereof.

In certain exemplary, non-limiting embodiments, a topical cannabinoid composition provided herein may retain a pH within a range of about 4 to about 7 while being cycled weekly between freezer and ambient room temperature conditions for a minimum of 1 month.

In certain exemplary, non-limiting embodiments, a topical cannabinoid composition provided herein may, when applied to a 0.45 μm cellulose acetate membrane mounted in a Franz cell, have a cannabinoid diffusion rate of about 14 $\mu g/cm^2/h$ to about 95 $\mu g/cm^2/h$.

In certain exemplary, non-limiting embodiments, a topical cannabinoid composition provided herein may, when applied to a membrane comprising lipid-impregnated polyethersulfone and polyolefin layers mounted in a Franz cell, has a cannabinoid diffusion rate increased from 150-200% as compared to the control (42 $\mu g/cm^2$ as compared to 20 $\mu g/cm^2$).

It is understood that the amount of cannabinoid necessary to achieve a desired therapeutic result is influenced by, and will therefore vary based on, a number of factors, including for example and without limitation, the age, sex, and weight of the subject, factors that influence the metabolic rate, and the specific disorders, diseases or related treatment symptoms of the subject. The concentration of at least one cannabinoid in compositions provided herein is between about 0.002% and about 10%.

One of skill in the art will understand that the ingredients in the final formulations must total 100% and, based on the teachings provided herein, will understand that modifications to the exemplary formulations provided herein are possible (e.g., replacement of a recited ingredient with a different ingredient, addition of a different ingredient, and/or modification of an amount of an ingredient) provided that such modifications result in a formulation as taught and described herein (i.e., capable of delivering an active agent such as a cannabinoid topically).

In another aspect, there is provided a method of applying a topical cannabinoid composition provided herein to the skin areas of a subject affected by inflammation and/or pain associated with musculoskeletal disease or condition. Application may be carried out by dropping, spraying, diffusing, dispersing, squirting, or spreading the composition, and may optionally be carried out using an applicator, such as a dropper, a nebulizer, an impregnated gauze sheet, a syringe, a patch, or a cotton swab.

In another aspect, there is provided a method of treating inflammation and/or pain associated with a musculoskeletal disease or condition in a subject, comprising applying a topical cannabinoid composition provided herein to the affected skin areas of a subject. The skin areas of a subject are knee joints; proximal interphalangeal (PIP) and metacarpophalangeal (MCP) joints of the hands; wrist joints; small joints of the feet including the metatarsophalangeal (MTP) joints; shoulder joints; elbow joints; neck joints; rib cage; upper back; lower back; hips; buttocks; thighs; ankle joints; heels and toes.

In another aspect, there is provided a use of a topical cannabinoid composition provided herein for the treatment of inflammation and/or pain associated with a musculoskeletal disease or condition in a subject.

In certain exemplary, non-limiting embodiments, the musculoskeletal disease or condition is: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

Still further embodiments of the present disclosure relate to providing a kit, which may include a container containing a topical cannabinoid composition provided herein, or a number of containers containing materials for preparing the topical cannabinoid composition. The kit may also include instructions for treating the inflammation and/or pain associated with the musculoskeletal disease or condition using the topical cannabinoid composition including dosage and how the composition may be applied to the skin. When separate containers are provided in the kit, and depending on the contents in these containers, the kit may also include instructions for preparing a topical cannabinoid composition, or compositions with different concentrations of active ingredients, from the materials included in the kit and optionally other materials such as a carrier or other additives. The kit may further include an applicator for applying the topical cannabinoid composition to the skin of a subject and may include specific instructions on how to use the applicator.

In certain exemplary, non-limiting embodiments, a topical cannabinoid composition provided herein may be prepared or obtained from a kit comprising (a) one or more cannabinoids; (b) one or more humectants; (c) one or more penetration enhancers; (d) a liquid carrier selected for application of the topical composition to the skin of a subject; and (e) instructions, wherein at least one of (a), (b) and (c) is not mixed with (d) in the kit, and wherein the instructions comprise information allowing all of (a), (b) and (c) be mixed with (d) at selected concentrations disclosed herein. The kit may include separate containers or instructions for providing or preparing more than one composition with different concentrations for one or more of (a), (b) and (c).

In certain exemplary, non-limiting embodiments, a kit may include a container containing a topical cannabinoid composition provided herein. The composition may be in form of cream, ointment, gel, liquid, patch, or the like as described above. The container may be, for example, a liquid bottle or a paste tube depending on the physical form of the composition. In other embodiments, a kit may include a plurality of containers containing materials for forming a topical cannabinoid composition provided herein. The kit may further comprise at least one of instructions for applying the composition to skin; instructions for using the composition to treat inflammation and/or pain associated with the musculoskeletal disease or condition according to the methods or uses provided herein; and instructions for using the materials in the plurality of containers to prepare the composition according to the methods of preparation provided herein. Optional components of a kit may include one or more applicators (such as droppers, sprayers, gauze sheets, patch, and cotton-tipped applicators) for applying the composition to skin. The one or more applicators may be sterilized and contained in a sealed sterile packaging.

The discussion herein and the following examples set forth and illustrate various exemplary embodiments of the present disclosure, which are understood to be illustrative and non-limiting.

NON-LIMITING EMBODIMENTS

Particular embodiments of the disclosure include, without limitation, the following:
1. A topical cannabinoid composition comprising:
   a. a cannabinoid at 0.01-10% (w/w),
   b. a humectant at 0.01-10% (w/w),
   c. a penetration enhancer at 1-5% (w/w), and
   d. water to make up 100% by weight,
   wherein the topical cannabinoid composition comprises less than 10% (w/w) of glycol ether.
2. The topical cannabinoid composition of embodiment 1, wherein the topical cannabinoid composition comprises less than 9%, less than 5%, less than 1%, less than 0.5%, or less than 0.25% (w/w) of glycol ether.
3. The topical cannabinoid composition of embodiment 1 or 2, wherein the topical cannabinoid composition comprises less than 5% (w/w) of glycol ether.
4. The topical cannabinoid composition of embodiment 3, wherein the topical cannabinoid composition comprises less than 0.5% (w/w) of glycol ether.
5. A topical cannabinoid composition comprising:
   a. a cannabinoid at 0.01-10% (w/w),
   b. a humectant at 0.01-10% (w/w),
   c. a penetration enhancer at 1-5% (w/w), and
   d. water at no less than 31% (w/w).
6. The topical cannabinoid composition of any one of embodiments 1 to 5, which comprises about 0.01% (w/w) of the cannabinoid.
7. The topical cannabinoid composition of any one of embodiments 1 to 5, which comprises about 0.1% (w/w) of the cannabinoid.
8. The topical cannabinoid composition of any one of embodiments 1 to 5, which comprises about 0.5% (w/w) of the cannabinoid.
9. The topical cannabinoid composition of any one of embodiments 1 to 5, which comprises about 1% (w/w) of the cannabinoid.
10. The topical cannabinoid composition of any one of embodiments 1 to 5, which comprises about 2% (w/w) of the cannabinoid.
11. The topical cannabinoid composition of any one of embodiments 1 to 5, which comprises about 3% (w/w) of the cannabinoid.
12. The topical cannabinoid composition of any one of embodiments 1 to 5, which comprises about 4% (w/w) of the cannabinoid.
13. The topical cannabinoid composition of any one of embodiments 1 to 5, which comprises about 5% (w/w) of the cannabinoid.
14. The topical cannabinoid composition of any one of embodiments 1 to 5, which comprises about 6% (w/w) of the cannabinoid.
15. The topical cannabinoid composition of any one of embodiments 1 to 5, which comprises about 7% (w/w) of the cannabinoid.
16. The topical cannabinoid composition of any one of embodiments 1 to 5, which comprises about 8% (w/w) of the cannabinoid.
17. The topical cannabinoid composition of any one of embodiments 1 to 5, which comprises about 9% (w/w) of the cannabinoid.
18. The topical cannabinoid composition of any one of embodiments 1 to 5, which comprises about 10% (w/w) of the cannabinoid.
19. The topical cannabinoid composition of any one of embodiments 1 to 18, wherein the cannabinoid is cannabidiol (CBD), cannabidiolic acid (CBDA), cannabidivarin (CBDV), cannabigerol (CBG), cannabigervarin (CBGV), tetrahydrocannabivarin (THCV), or tetrahydrocannabinol (THC), or any combination thereof.
20. The topical cannabinoid composition of embodiment 19, wherein the cannabinoid is cannabidiol (CBD).
21. The topical cannabinoid composition of any one of the embodiments 1 to 20, which comprises about 0.01% (w/w) of the humectant.
22. The topical cannabinoid composition of any one of the embodiments 1 to 20, which comprises about 0.1% (w/w) of the humectant.
23. The topical cannabinoid composition of any one of the embodiments 1 to 20, which comprises about 0.5% (w/w) of the humectant.
24. The topical cannabinoid composition of any one of the embodiments 1 to 20, which comprises about 1% (w/w) of the humectant.
25. The topical cannabinoid composition of any one of the embodiments 1 to 20, which comprises about 2% (w/w) of the humectant.
26. The topical cannabinoid composition of any one of the embodiments 1 to 20, which comprises about 3% (w/w) of the humectant.
27. The topical cannabinoid composition of any one of the embodiments 1 to 20, which comprises about 4% (w/w) of the humectant.
28. The topical cannabinoid composition of any one of the embodiments 1 to 20, which comprises about 5% (w/w) of the humectant.
29. The topical cannabinoid composition of any one of the embodiments 1 to 20, which comprises about 6% (w/w) of the humectant.
30. The topical cannabinoid composition of any one of the embodiments 1 to 20, which comprises about 7% (w/w) of the humectant.

31. The topical cannabinoid composition of any one of the embodiments 1 to 20, which comprises about 8% (w/w) of the humectant.
32. The topical cannabinoid composition of any one of the embodiments 1 to 20, which comprises about 9% (w/w) of the humectant.
33. The topical cannabinoid composition of any one of the embodiments 1 to 20, which comprises about 10% (w/w) of the humectant.
34. The topical cannabinoid composition of any one of embodiments 1 to 33, wherein the humectant has a molecular weight lower than the molecular weight of the cannabinoid.
35. The topical cannabinoid composition of any one of embodiments 1 to 34, wherein the humectant is a polyol.
36. The topical cannabinoid composition of embodiment 35, wherein the polyol is glycerin, propylene glycol, butylene glycol, dipropylene glycol, pentylene glycol, hexylene glycol, polyethylene glycol, or any combination thereof.
37. The topical cannabinoid composition of embodiment 36, wherein the humectant is 1,3-butylene glycol.
38. The topical cannabinoid composition of any one of the embodiments 1 to 37, which comprises about 1% (w/w) of the penetration enhancer.
39. The topical cannabinoid composition of any one of the embodiments 1 to 37, which comprises about 2% (w/w) of the penetration enhancer.
40. The topical cannabinoid composition of any one of the embodiments 1 to 37, which comprises about 3% (w/w) of the penetration enhancer.
41. The topical cannabinoid composition of any one of the embodiments 1 to 37, which comprises about 4% (w/w) of the penetration enhancer.
42. The topical cannabinoid composition of any one of the embodiments 1 to 37, which comprises about 5% (w/w) of the penetration enhancer.
43. The topical cannabinoid composition of any one of embodiments 1 to 42, wherein penetration enhancer has a molecular weight lower than the molecular weight of the cannabinoid.
44. The topical cannabinoid composition of any one of embodiments 1 to 43, wherein the penetration enhancer is a glycol ether, octyldecanol, isopropyl myristate, or any combination thereof.
45. The topical cannabinoid composition of embodiment 44, wherein the penetration enhancer is a glycol ether selected from diethylene glycol monoethyl ether, steareth-20, and steareth-2, or is any combination thereof.
46. The topical cannabinoid composition of embodiment 45, wherein the penetration enhancer is diethylene glycol monoethyl ether.
47. The topical cannabinoid composition of any one of embodiments 1 to 46, wherein both the humectant and the penetration enhancer have a molecular weight lower than the molecular weight of the cannabinoid.
48. The topical cannabinoid composition of any one of embodiments 1 to 47, wherein the humectant is 1,3-butylene glycol, and the penetration enhancer is diethylene glycol monoethyl ether.
49. The topical cannabinoid composition of any one of embodiments 1 to 48, wherein the composition further comprises an emulsifier at 1-10% (w/w).
50. The topical cannabinoid composition of embodiment 49, wherein the emulsifier is carboxymethyl cellulose, or hydroxyethyl cellulose; polyacrylates such as carbomer or carbopol (e.g. Carbopol® 974); polycarbophils such as Noveon® AA-1; polyvinylalcohol such as Mowiol® 26-88; polyvinylpyrrolidone such as Povidone® K30; xanthan gum; acryloyldimethyltaurate polymers such as acrylamide/sodium acryloyldimethyltaurate copolymer (e.g. Sepineo® P600), acrylamide/sodium acryloyldimethyltaurate/acrylic acid copolymer, ammonium acryloyldimethyltaurate/Beheneth-25 methacrylate crosspolymer, ammonium acryloyldimethyltaurate/carboxyethyl acrylate crosspolymer, ammonium acryloyldimethyltaurate/Laureth-7 methacrylate copolymer, ammonium acryloyldimethyltaurate/Steareth-25 methacrylate crosspolymer, ammonium acryloyldimethyltaurate/Steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium scryloyldimethyltaurate/Steareth-20 methacrylate copolymer, hydroxyethyl acrylate/sodium acryloyldimethyl taurate copolymer, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer, sodium polyacryloyldimethyl taurate, or any combination thereof.
51. The topical cannabinoid composition of embodiment 50, wherein the emulsifier is Sepineo® P600.
52. The topical cannabinoid composition of any one of embodiments 1 to 51, wherein the composition further comprises a surfactant at 0.5-5% (w/w).
53. The topical cannabinoid composition of embodiment 52, wherein the surfactant is a castor oil derivative, an ethoxylated fatty alcohol such as PEG-1000 monocetyl ether, alkyl trimethyl ammonium bromide, glycerol monostearate, potassium stearate, sodium lauryl sulfate, sodium cetearyl sulfate, saponin, Polysorbate 20 (Tween™ 20), Polysorbate 40 (Tween 40), Polysorbate 60 (Tween 60) and Polysorbate 80 (Tween 80), or any combination thereof.
54. The topical cannabinoid composition of embodiment 53, wherein the surfactant is Polysorbate 80 (Tween 80).
55. The topical cannabinoid composition of any one of embodiments 1 to 54, wherein the composition further comprises a second penetration enhancer at 0.1-3% (w/w).
56. The topical cannabinoid composition of embodiment 55, wherein the second penetration enhancer is an essential oil such as anise oil, angelica oil, basil oil, bay oil, bergamot oil, rose oil, camphor oil, cananga oil, cardamom oil, caraway oil, cedar oil, cedarwood oil, Chamaecyparis obtusa oil, chamomile oil, cinnamon oil, citronella oil, clove oil, copaiba balsam oil, cumin oil, clove oil, coriander oil, dill oil, eucalyptus oil, fennel oil, garlic oil, geranium oil, grapefruit oil, ginger oil, guaiac oil, hiba oil, iris oil, Japanese mint oil, jasmine oil, lavender oil, lemon oil, lemongrass oil, linaloe oil, Lindera oil, mandarin oil, mint oil, neroli oil, onion oil, orange oil, oregano oil, palmarosa sofia oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, vetivert oil, western mint oil, wintergreen oil, or any combination thereof.
57. The topical cannabinoid composition of embodiment 56, wherein the second penetration enhancer is clove oil.
58. The topical cannabinoid composition of any one of embodiments 1 to 57, wherein the composition further comprises a cooling sensation enhancer at 0.5-2.5% (w/w).
59. The topical cannabinoid composition of embodiment 58, wherein the cooling sensation enhancer is menthol, menthyl acetate, menthone, isomentone, sabinene hydrate, isopulegol, piperitol, p-menthane-3-carboxylic acid amide, p-menthanediol, menthylglucoside, menthyl-2-pyrrolidone-5 Carboxylate, menthyl keto alkanoate, menthyl N-acetylglycine, menthyl hydroxyalkanoate, 2-mentoxytetrahydropyran, 2-mentoxytetrahydrofuran, menthoxypropane-1,2-diol, menthyl 3-hydroxybutyrate, or any combination thereof.
60. The topical cannabinoid composition of embodiment 59, wherein the cooling sensation enhancer is menthol.
61. The topical cannabinoid composition of any of embodiments 1 to 60, wherein the composition further comprises a preservative at 0.1-3% (w/w).
62. The topical cannabinoid composition of embodiment 61, wherein the preservative is ethylparaben, methylparaben, propylparaben, butylparaben, isobutylparaben, benzalkonium chloride, imidurea, phenoxyethanol, or any combination thereof.
63. The topical cannabinoid composition of embodiment 62, wherein the preservative is phenoxyethanol.
64. The topical cannabinoid composition of any one of embodiments 1 to 63, wherein the composition further comprises an antioxidant at 0.1-3% (w/w).
65. The topical cannabinoid composition of embodiment 64, wherein the antioxidant is vitamin B, nordihydroguaiaretic acid, butylated hydroxyanisole (BHA), butylated hydroxytoluene (BHT), propyl gallate, erythorbate acid, sodium erythorbate, ascorbic palmitate, ascorbic stearate, or any combination thereof.
66. The topical cannabinoid composition of embodiment 65, wherein the antioxidant is butylated hydroxytoluene (BHT).
67. The topical cannabinoid composition of any one of embodiments 1 to 66, wherein the composition further comprises a third penetration enhancer at 1-5% (w/w).
68. The topical cannabinoid composition of embodiment 67, wherein the third penetration enhancer is isopropyl myristate, myristoleic acid, palmitoleic acid, sapienic acid, oleic acid, elaidic acid, vaccenic acid, linoleic acid, linoelaidic acid, arachidonic acid, eicosapentaenoic acid, erucic acid, docosahexaenoic acid, or any combination thereof.
69. The topical cannabinoid composition of embodiment 68, wherein the third penetration enahancer is oleic acid.
70. The topical cannabinoid composition of any one of embodiments 1 to 69, wherein the composition has a pH within the range of about 4 to about 7.
71. The topical cannabinoid composition of any one of embodiments 1 to 70, wherein the composition retains its viscosity and pH while being cycled weekly between freezer and ambient room temperature conditions for a minimum of 1 month.
72. The topical cannabinoid composition of any one of embodiments 1 to 71, wherein the composition, when applied to a 0.45 µm cellulose acetate membrane mounted in a Franz cell, has a cannabinoid diffusion rate of about 14 µg/cm$^2$/h to about 95 µg/cm$^2$/h.
73. The topical cannabinoid composition of any one of embodiments 1 to 72, wherein the composition, when applied to a membrane comprising lipid-impregnated polyethersulfone and polyolefin layers mounted in a Franz cell, has a cannabinoid diffusion rate increased from 150-200% as compared to the control (42 µg/cm$^2$ vs 20 µg/cm$^2$).
74. The topical cannabinoid composition of any one of embodiments 1 to 73, wherein the composition is a cream, ointment, gel, lotion, liquid, solution, spray, aerosol, patch, or any other dosage form suitable for topical application, or any combination thereof.
75. The topical cannabinoid composition of embodiment 74, wherein the composition is a gel.
76. A method comprising applying the topical cannabinoid composition of any one of embodiments 1 to 75 to the skin areas of a subject affected by inflammation and/or pain associated with musculoskeletal disease or condition.
77. The method of embodiment 76, wherein the skin areas of a subject are knee joints; proximal interphalangeal (PIP) and metacarpophalangeal (MCP) joints of the hands; wrist joints; small joints of the feet including the metatarsophalangeal (MTP) joints; shoulder joints; elbow joints; neck joints; rib cage; upper back; lower back; hips; buttocks; thighs; ankle joints; heels and toes.
78. The method of embodiment 76, wherein the musculoskeletal disease or condition is: rheumatoid arthritis; rheumatoid spondylitis; ankylosing spondylitis; osteoarthritis; spondylosi s deformans; gouty arthritis; juvenile arthritis; scapulohumeral periarthritis; cervical syndrome; lumbago; or lumbago accompanying spondylosis deformans.
79. The method of embodiment 78, wherein the musculoskeletal disease or condition is rheumatoid arthritis, osteoarthritis, juvenile arthritis, or gouty arthritis.
80. The method of embodiment 79, wherein the musculoskeletal disease or condition is osteoarthritis.
81. The method of embodiment 80, wherein the affected skin area is inflamed, reddened, ached, or sore.
82. The method of embodiment 81, wherein the affected skin area is painful, sensitive, swollen, or tender.
83. A method of treating a musculoskeletal disease or condition in a subject, comprising applying the topical cannabinoid composition of any one of embodiments 1 to 75 to the affected skin area of a subject.
84. The method of embodiment 83, wherein the musculoskeletal disease or condition is: rheumatoid arthritis; rheumatoid spondylitis; ankylosing spondylitis; osteoarthritis; spondylosi s deformans; gouty arthritis; juvenile arthritis; scapulohumeral periarthritis; cervical syndrome; lumbago; or lumbago accompanying spondylosis deformans.
85. The method of embodiment 84, wherein the musculoskeletal disease or condition is rheumatoid arthritis, osteoarthritis, juvenile arthritis, or gouty arthritis.
86. The method of embodiment 85, wherein the musculoskeletal disease or condition is osteoarthritis.

87. The method of embodiment 86, wherein the affected skin area is inflamed, reddened, ached, or sore.
88. The method of embodiment 87, wherein the affected skin area is painful, sensitive, swollen, or tender.
89. The method of any one of embodiments 76 to 88, wherein the applying comprises dropping, spraying, diffusing, dispersing, squirting, or spreading the composition.
90. The method of any one of embodiments 76 to 89, wherein the subject is a mammal.
91. The method of any one of embodiments 76 to 90, wherein the subject is a companion animal.
92. The method of embodiment 90, wherein the subject is a human.
93. The method of any one of embodiments 76 to 92, wherein the method further comprises administering an additional therapy for a musculoskeletal disease or condition.
94. Use of the topical cannabinoid formulation of any one of embodiments 1 to 75 for the treatment of a musculoskeletal disease or condition in a subject.
95. The use of embodiment 94, wherein the musculoskeletal disease or condition is: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.
96. The use of embodiment 95, wherein the musculoskeletal disease or condition is is rheumatoid arthritis, osteoarthritis, juvenile arthritis, or gouty arthritis.
97. The use of embodiment 96, wherein the musculoskeletal disease or condition is osteoarthritis.
98. The use of embodiment 94, wherein the affected skin area is inflamed, reddened, ached, or sore.
99. The use of embodiment 94, wherein affected skin area is painful, sensitive, swollen, or tender.
100. The use of any of embodiments 94 to 99, wherein the subject is a mammal.
101. The use of any of embodiments 94 to 100, wherein the subject is a companion animal.
102. The use of embodiment 100, wherein the subject is a human.
103. The use of any one of embodiments 94 to 102, wherein the treatment further comprises an additional therapy for a musculoskeletal disease or condition.
104. A kit comprising a container containing the topical cannabinoid composition of any one of embodiments 1 to 75.
105. A kit comprising a plurality of containers containing materials for forming the topical cannabinoid composition of any one of embodiments 1 to 75.
106. The kit of embodiment 104 or 105, further comprising instructions for preparing the topical cannabinoid composition from the materials in the containers.
107. The kit of any one of embodiments 104 to 106, further comprising instructions for applying the topical cannabinoid composition to the affected skin area of a subject.
108. The kit of any one of embodiments 104 to 107, further comprising instructions for using the topical cannabinoid composition to treat a musculoskeletal disease or condition according to the method of any one of embodiments 76 to 93.
109. The kit of any one of embodiments 104 to 108, further comprising one or more applicators for applying the topical cannabinoid composition to the affected skin area of a subject.
110. A topical cannabinoid composition comprising:
   a) a cannabinoid at 0.01-10% (w/w),
   b) a humectant at 0.01-10% (w/w),
   c) a penetration enhancer at 1-5% (w/w),
   d) an emulsifier at 1-10% (w/w),
   e) a surfactant at 0.5-5% (w/w),
   f) a second penetration enhancer at 0.1-3% (w/w),
   g) a cooling sensation enhancer at 0.5-2.5% (w/w),
   h) a preservative at 0.1-3% (w/w),
   i) an antioxidant at 0.1-3% (w/w),
   j) a third penetration enhancer at 1-5% (w/w), and
   k) water to make up 100% by weight.
111. The topical cannabinoid composition of embodiment 110, wherein said cannabinoid is cannabidiol (CBD), cannabidiolic acid (CBDA), cannabidivarin (CBDV), cannabigerol (CBG), cannabigervarin (CBGV), tetrahydrocannabivarin (THCV), or tetrahydrocannabinol (THC).
112. The topical cannabinoid composition of embodiment 111, wherein said cannabinoid is CBD.
113. The topical cannabinoid composition of embodiment 110, wherein said humectant is glycerin, propylene glycol, butylene glycol, dipropylene glycol, pentylene glycol, hexylene glycol or polyethylene glycol.
114. The topical cannabinoid composition of embodiment 113, wherein said humectant is 1,3-butylene glycol.
115. The topical cannabinoid composition of embodiment 110, wherein said penetration enhancer is diethylene glycol monoethyl ether, steareth-20, steareth-2, octyldecanol or isopropyl myristate.
116. The topical cannabinoid composition of embodiment 115, wherein said penetration enhancer is diethylene glycol monoethyl ether.
117. The topical cannabinoid composition of embodiment 110, wherein said emulsifier is carboxymethyl cellulose, or hydroxyethyl cellulose; polyacrylates such as carbomer or carbopol (e.g. Carbopol® 974); polycarbophils such as Noveon® AA-1; polyvinylalcohol such as Mowiol® 26-88; polyvinylpyrrolidone such as Povidone® K30; xanthan gum; acryloyldimethyltaurate polymers such as acrylamide/sodium acryloyldimethyltaurate copolymer (e.g. Sepineo® P600), acrylamide/sodium acryloyldimethyltaurate/acrylic acid copolymer, ammonium acryloyldimethyltaurate/Beheneth-25 methacrylate crosspolymer, ammonium acryloyldimethyltaurate/carboxyethyl acrylate crosspolymer, ammonium acryloyldimethyltaurate/Laureth-7 methacrylate copolymer, ammonium acryloyldimethyltaurate/Steareth-25 methacrylate crosspolymer, ammonium acryloyldimethyltaurate/Steareth-8 methacrylate copolymer, ammonium acryloyldimethyltaurate/vinyl formamide copolymer, ammonium acryloyldimethyltaurate/VP copolymer, ammonium polyacryloyldimethyl taurate, dimethylacrylamide/sodium acryloyldimethyltaurate crosspolymer, HEA/sodium scryloyldimethyltaurate/Steareth-20 methacrylate copolymer, hydroxyethyl acrylate/sodium acryloyldimethyl taurate copolymer, sodium acrylate/acryloyldimethyltaurate/dimethylacrylamide crosspolymer, sodium acrylate/sodium acryloyldimethyl taurate copolymer, sodium acrylate/sodium acryloyldimethyl taurate/acrylamide copolymer, sodium acryloyl dimethyl taurate/PEG-8 diacrylate crosspolymer, sodium acryloyldimethyl taurate/acrylamide/VP copolymer, sodium acryloyldimethyltaurate/methacrylamidolauric acid copolymer, sodium acryloyldimethyltaurate/VP crosspolymer or sodium polyacryloyldimethyl taurate.

118. The topical cannabinoid composition of embodiment 117, wherein said emulsifier is Sepineo® P600.

119. The topical cannabinoid composition of embodiment 110, wherein said surfactant is a castor oil derivative, an ethoxylated fatty alcohol such as PEG-1000 monocetyl ether, alkyl trimethyl ammonium bromide, glycerol monostearate, potassium stearate, sodium lauryl sulfate, sodium cetearyl sulfate, saponin, Polysorbate 20 (Tween™ 20), Polysorbate 40 (Tween 40), Polysorbate 60 (Tween 60) or Polysorbate 80 (Tween 80).

120. The topical cannabinoid composition of embodiment 119, wherein said surfactant is Polysorbate 80 (Tween 80).

121. The topical cannabinoid composition of embodiment 110, wherein said second penetration enhancer is an essential oil such as anise oil, angelica oil, basil oil, bay oil, bergamot oil, rose oil, camphor oil, cananga oil, cardamom oil, caraway oil, cedar oil, cedarwood oil, Chamaecyparis obtusa oil, chamomile oil, cinnamon oil, citronella oil, clove oil, copaiba balsam oil, cumin oil, clove oil, coriander oil, dill oil, eucalyptus oil, fennel oil, garlic oil, geranium oil, grapefruit oil, ginger oil, guaiac oil, hiba oil, iris oil, Japanese mint oil, jasmine oil, lavender oil, lemon oil, lemongrass oil, linaloe oil, Lindera oil, mandarin oil, mint oil, neroli oil, onion oil, orange oil, oregano oil, palmarosa sofia oil, patchouli oil, parsley oil, pepper oil, peppermint oil, perilla oil, Peru balsam oil, petitgrain oil, pine oil, pine needle oil, rose oil, rosemary oil, sandalwood oil, spearmint oil, star anis oil, sweet orange oil, tangerine oil, tea seed oil, tea tree oil, thyme oil, tolu balsam oil, tuberose oil, turmeric oil, vetivert oil, western mint oil or wintergreen oil.

122. The topical cannabinoid composition of embodiment 121, wherein said second penetration enhancer is clove oil.

123. The topical cannabinoid composition of embodiment 110, wherein said cooling sensation enhancer is menthol, menthyl acetate, menthone, isomentone, sabinene hydrate, isopulegol, piperitol, p-menthane-3-carboxylic acid amide, p-menthanediol, menthylglucoside, menthyl-2-pyrrolidone-5 Carboxylate, menthyl keto alkanoate, menthyl N-acetylglycine, menthyl hydroxyalkanoate, 2-mentoxytetrahydropyran, 2-mentoxytetrahydrofuran, menthoxypropane-1,2-diol or menthyl 3-hydroxybutyrate.

124. The topical cannabinoid composition of embodiment 123, wherein said cooling sensation enhancer is menthol.

125. The topical cannabinoid composition of embodiment 110, wherein said preservative is ethylparaben, methylparaben, propylparaben, butylparaben, isobutylparaben, benzalkonium chloride, imidurea or phenoxyethanol.

126. The topical cannabinoid composition of embodiment 125, wherein said preservative is phenoxyethanol.

127. The topical cannabinoid composition of embodiment 110, wherein said antioxidant is vitamin B, nordihydroguaiaretic acid, butylated hydroxyanisole (BHA), butylated hydroxytoluene (BHT), propyl gallate, erythorbate acid, sodium erythorbate, ascorbate palmitate or ascorbate stearate.

128. The topical cannabinoid composition of embodiment 127, wherein said antioxidant is butylated hydroxytoluene (BHT).

129. The topical cannabinoid composition of embodiment 110, wherein said third penetration enhancer is isopropyl myristate, myristoleic acid, palmitoleic acid, sapienic acid, oleic acid, elaidic acid, vaccenic acid, linoleic acid, linoelaidic acid, arachidonic acid, eicosapentaenoic acid, erucic acid or docosahexaenoic acid.

130. The topical cannabinoid composition of embodiment 129, wherein said stabilizing agent is oleic acid.

131. The topical cannabinoid composition of embodiment 110, wherein the said composition has a pH within the range of about 4 to 7.

132. The topical cannabinoid composition of embodiment 110, wherein the said composition has a very high rate of transdermal diffusion as measured using in-vitro Franz diffusion cell assays.

133. The topical cannabinoid composition of embodiment 110, wherein the said composition has very strong penetration capacity and very high absorption into the deeper tissues of the skin.

134. The topical cannabinoid composition of embodiment 110, wherein the said composition is a topical gel composition.

135. The topical cannabinoid composition of any one of embodiments 110 to 134, wherein the composition is useful for the treatment of inflammation and/or pain associated with one or more musculoskeletal diseases such as: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

136. A gel comprising:
   a. a cannabinoid at 0.01-10% (w/w),
   b. a cannabinoid deep penetration aiding agent at 0.1-10% (w/w), and
   c. water to make up 100% by weight.

The following examples are provided to illustrate certain particular features and/or embodiments. These examples should not be construed to limit the disclosure to the particular features or embodiments described.

NON-LIMITING EXAMPLES

Example 1. Topical cannabinoid compositions: This example provides an overview of embodiments of the deep penetrating cannabinoid compositions (Tables 1 & 2) described herein, which are useful in the treatment of inflammation and/or pain associated with musculoskeletal diseases.

TABLE 1

| | Composition A | |
|---|---|---|
| Phase | Ingredient | w/w % |
| Emulsion Phase (A) | Aqua | Q.S. |
| Polymer Phase (B) | Sepineo ™ P600 | 3.00 |
| Oil Phase | Isopropyl myristate | 2.50 |

TABLE 1-continued

Composition A

| Phase | Ingredient | w/w % |
|---|---|---|
| (C) | Menthol | 1.25 |
| | Diethylene glycol monoethyl ether | 2.50 |
| | Phenoxyethanol | 0.50 |
| | Polysorbate 80 | 2.50 |
| | Clove Oil | 0.50 |
| | Cannabidiol | 0.5-3.5 |
| Total | | 100.0% |

TABLE 2

Composition B

| Phase | Ingredient | w/w % |
|---|---|---|
| Emulsion Phase (A) | Aqua | Q.S. |
| Polymer Phase (B) | Sepineo ™ P600 | 3.00 |
| Oil Phase (C) | Butylated hydroxytoluene (BHT) | 0.25 |
| | Oleic acid | 3.00 |
| | Menthol | 1.25 |
| | Diethylene glycol monoethyl ether | 2.50 |
| | Phenoxyethanol | 0.25 |
| | Polysorbate 80 | 3.00 |
| | 1,3 Butylene Glycol | 4.00 |
| | Clove Oil | 0.50 |
| | Cannabidiol | 0.5-3.5 |
| Total | | 100.0% |

Example 2. Characterization and diffusion profile of the compositions described in Example 1.

To enhance the transdermal diffusion of the cannabinoids through the skin, the compositions described in Example 1 were developed by encapsulating cannabinoids within nano- and micro-metric emulsion system and then stabilized in a gel matrix with the addition of several known penetration enhancers. The characterization of the composition included phase separation, pH, rheological, and diffusion analyses (cellulose membranes) was performed to ensure quality and robustness of the product. Additional Franz cell assessments with Strat-M® technology were effectuated to estimate the relative CBD diffusion in comparison to the control formulations.

Four formulations containing 0.5, 1, 2, and 3.5% CBD w/w having similar excipients were developed and stability studies including pH measurement, viscosity, and Franz cell diffusion analysis was performed (FIG. 1). pH values and viscosity analysis confirmed that all formulations remained within the specifications and higher CBD content does not affect the stability of the finished products. No phase separation was observed after incubation of the products at 50° C. for 1 hour followed by centrifugation at 3500 rpm for a period of 30 minutes.

Figure 2:
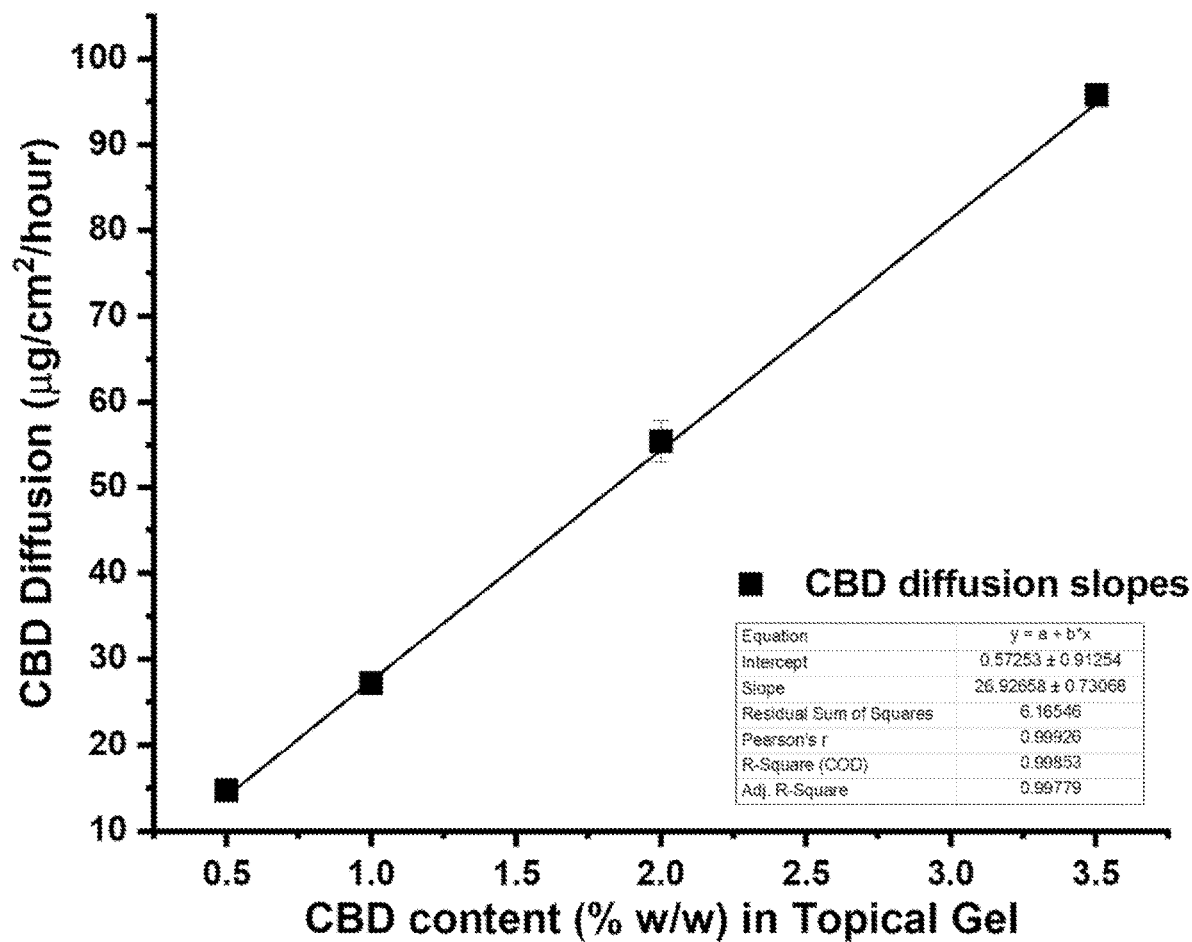
FIG. 2 illustrates plot of the average CBD diffusion rate ($\mu g/cm^2/h$) of composition A through cellulose acetate membrane according to the CBD content.

The mean release rates for 0.5%, 1.0%, 2.0% and 3.5% CBD formulations were 14.45 $\mu g/cm^2/h$, 27.24 $\mu g/cm^2/h$, 55.45 $\mu g/cm^2/h$ and 94.85 $\mu g/cm^2/h$, respectively, and a linear relationship ($R^2=0.9996$) was observed between the release rates of the different strengths of CBD formulations (FIG. 2). This suggests that the diffusion of the "encapsulated CBD" through the cellulose acetate membrane remains linear and proportional to the CBD content infused and the gel matrix controlled the diffusion rate. No plateau was observed within this range of CBD.

Example 3. Franz Cell Assessment: StartM® Membrane Franz cell studies were performed on the compositions described in Table 2 in comparison with a control composition (Table 2) having propylene glycol as emulsifier, isopropyl myristate as stabilizing agent and was devoid of oleic acid and BHT.

Figure 3:
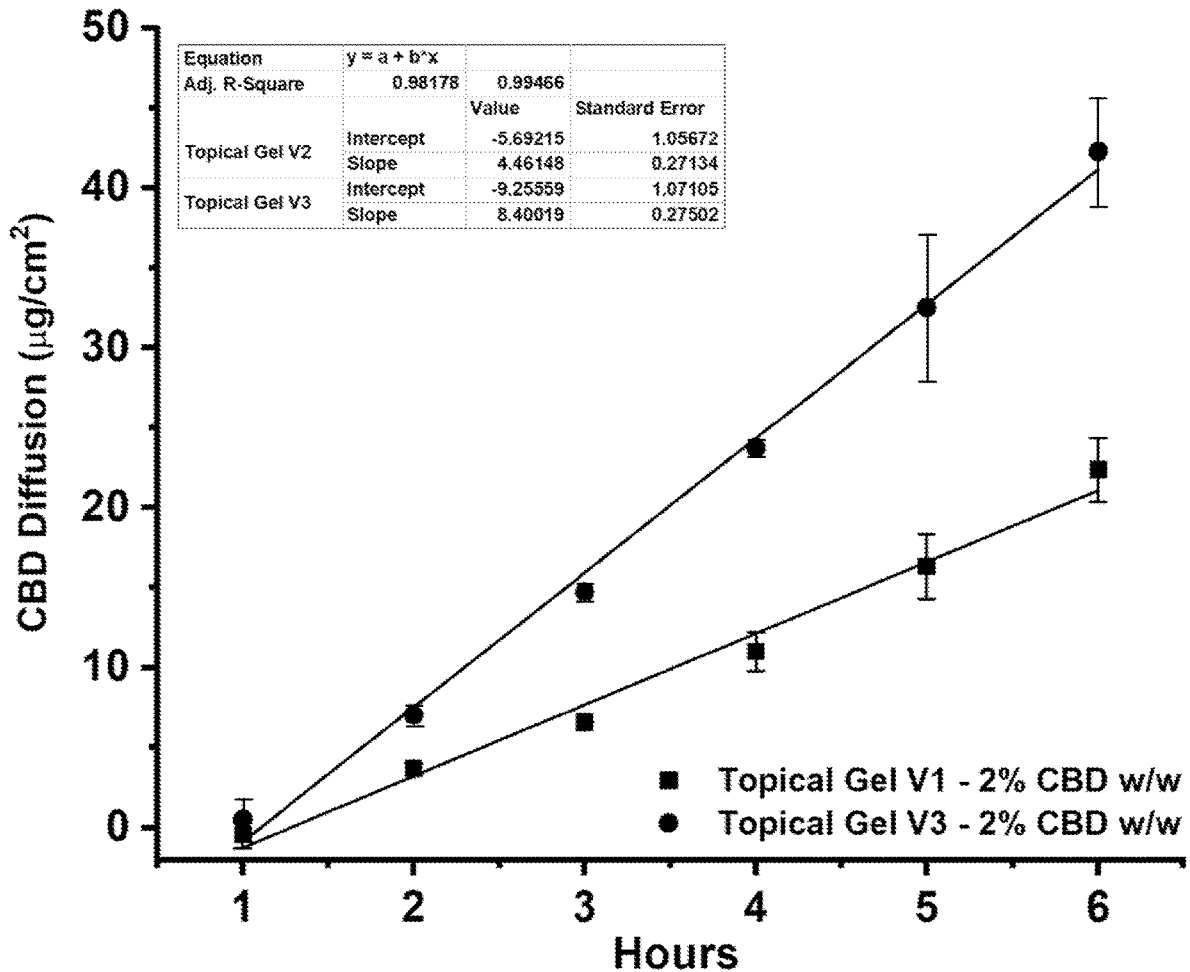
FIG. 3 illustrates CBD diffusion/release from the composition B (DTG-V3-2%) as compared to the control. CBD diffusion/release obtained under sink conditions through Strat-M® membrane at 36° C.-600 rpm. (n=6 for each evaluation).

In comparison to the control, mean CBD diffusion rate of the composition described in Table 2 was significantly increased when tested at 2% CBD (w/w) (FIG. 3). With the new combination of ingredients, the mean CBD diffusion increased by 175% as compared to the control. The diffusion rates were 20 $\mu g/cm^2$ for the control formulation and 42 $\mu g/cm^2$ for the composition described in Example 1 when loaded at 2% CBD.

While the foregoing has presented specific embodiments of the present disclosure, it is to be understood that these embodiments have been presented by way of example only. It is expected that others skilled in the art will perceive variations which, while varying from the foregoing, do not depart from the spirit and scope of the disclosure herein.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this disclosure belongs.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to encompass the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items.

As used herein, whether in the specification or the appended claims, the transitional terms "comprising", "including", "having", "containing", "involving", and the like are to be understood as being inclusive or open-ended (i.e., to mean including but not limited to), and they do not exclude unrecited elements, materials or method steps. Only the transitional phrases "consisting of" and "consisting essentially of", respectively, are closed or semi-closed transitional phrases with respect to claims and exemplary embodiment paragraphs herein. The transitional phrase "consisting of" excludes any element, step, or ingredient which is not specifically recited. The transitional phrase "consisting essentially of" limits the scope to the specified elements, materials or steps and to those that do not materially affect the basic characteristic(s) of the disclosure herein.

The invention claimed is:

1. A topical cannabinoid composition comprising a cannabinoid at 0.1-10% (w/w), a humectant at 0.01-10% (w/w), a penetration enhancer at 1-5% (w/w), an emulsifier at 1-10% (w/w) and water to make up 100% by weight wherein the topical cannabinoid composition comprises less than 10% (w/w) of glycol ether.

2. The topical cannabinoid composition of claim 1, wherein the topical cannabinoid composition comprises no more than 5% (w/w) of glycol ether.

3. The topical cannabinoid composition of claim 1, wherein the cannabinoid is selected from the group consisting of tetrahydrocannabinol (THC), tetrahydrocannabinolic acid (THCA), cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigervarin (CBGV), cannabigerol monomethyl ether (CBGM), cannabielsoin (CBE), cannabicitran (CBT), and any combinations thereof.

4. The topical cannabinoid composition of claim 3, wherein the cannabinoid is cannabidiol (CBD).

5. The topical cannabinoid composition of claim 1, wherein the humectant is selected from the group consisting of glycerin, propylene glycol, 1,3-butylene glycol, dipropylene glycol, pentylene glycol, hexylene glycol, polyethylene glycol, and any combinations thereof.

6. The topical cannabinoid composition of claim 5, wherein the humectant is 1,3-butylene glycol.

7. The topical cannabinoid composition of claim 1, wherein the penetration enhancer is selected from the group consisting of diethylene glycol monoethyl ether, steareth-20, steareth-2, octyldecanol, isopropyl myristate, and any combinations thereof.

8. The topical cannabinoid composition of claim 7, wherein the penetration enhancer is diethylene glycol monoethyl ether.

9. The topical cannabinoid composition of claim 1, wherein the emulsifier is selected from the group consisting of carboxymethyl cellulose, hydroxyethyl cellulose, polyacrylates, polycarbophils, polyvinylalcohol, polyvinylpyrrolidone, xanthan gum, acryloyldimethyltaurate polymers, and any combinations thereof.

10. The topical cannabinoid composition of claim 9, wherein the emulsifier is an acrylamide/sodium acryloyldimethyltaurate copolymer.

11. The topical cannabinoid composition of claim 1, wherein the composition further comprises a surfactant at 0.5-5% (w/w), a second penetration enhancer at 0.1-3% (w/w), a cooling sensation enhancer at 0.5-2.5% (w/w), a preservative at 0.1-3% (w/w), an antioxidant at 0.1-3% (w/w), a stabilizing agent at 1-5% (w/w), and water to make up 100% by weight.

12. The topical cannabinoid composition of claim 11, wherein the surfactant is Polysorbate 80, the second penetration enhancer is clove oil, the cooling sensation enhancer is menthol, the preservative is phenoxyethanol, the antioxidant is butylated hydroxytoluene (BHT), and the stabilizing agent is oleic acid.

13. The topical cannabinoid composition of claim 1, which has a pH of 5-7.

14. The topical cannabinoid composition of claim 1, wherein the composition is a cream, ointment, gel, lotion, liquid, solution, spray, aerosol, any other dosage forms suitable for topical application, or any combination thereof.

15. The topical cannabinoid composition of claim 14, wherein the composition is a gel.

16. The topical cannabinoid composition of claim 1, when applied to a membrane comprising lipid-impregnated polyethersulfone and polyolefin layers mounted in a Franz cell, has a cannabinoid diffusion rate of 25-60 µg/cm$^2$.

17. A method comprising applying the topical cannabinoid composition of claim 1 to the to the skin areas of a subject affected by inflammation and/or pain associated with musculoskeletal disease or condition.

18. The method of claim 17, wherein the musculoskeletal disease or condition is: rheumatoid arthritis; rheumatoid spondylitis; ankylosing spondylitis; osteoarthritis; spondylosis deformans; gouty arthritis; juvenile arthritis; scapulohumeral periarthritis; cervical syndrome; lumbago; or lumbago accompanying spondylosis deformans.

19. The topical cannabinoid composition of claim 1, wherein the composition encapsulates the cannabinoid within a nano- or micro-metric emulsion system in a gel matrix.

20. The topical cannabinoid composition of claim 10, wherein the acrylamide/sodium acryloyldimethyltaurate copolymer emulsifier is a dispersion of acrylamide/sodium acryloyldimethyl taurate copolymer in isohexadecane.

* * * * *